United States Patent [19]
Schaller et al.

[11] Patent Number: 4,894,332
[45] Date of Patent: Jan. 16, 1990

[54] **DNA SEQUENCES CODING FOR *MYCOPLASMA HYPOPNEUMONIAE* SURFACE ANTIGENS, METHODS OF USE TO MAKE THE CORRESPONDING PROTEINS**

[75] Inventors: Heinz E. Schaller; Mo-Quen Klinkert, both of Heidelberg, Fed. Rep. of Germany

[73] Assignee: Biogen, Inc., Cambridge, Mass.

[21] Appl. No.: 716,564

[22] Filed: Mar. 27, 1985

[51] Int. Cl.$^4$ .................. C12P 21/00; C12P 21/02; C12N 15/00; C12N 7/00
[52] U.S. Cl. ........................... 435/69.3; 435/172.3; 435/254; 435/255; 435/240.1; 435/240.2; 435/240.4; 435/252.31; 435/252.33; 435/252.34; 536/27; 935/12; 935/65
[58] Field of Search .............. 435/68, 70, 172.3, 255, 435/253, 240, 317.1, 354, 240.1, 240.2, 240.4; 935/12, 31, 38, 42, 43, 58, 65, 73, 81; 530/350, 806, 820, 821; 536/27

[56] References Cited

U.S. PATENT DOCUMENTS 4,530,901  7/1985  Weissman ........................... 435/70

FOREIGN PATENT DOCUMENTS 0024493   3/1981  European Pat. Off. ............. 435/68
0040922  12/1981  European Pat. Off. ............. 435/68
0090581  10/1983  European Pat. Off. ............. 435/68

OTHER PUBLICATIONS

Remaut et al., *Gene*, vol. 15, pp. 81–93, 1981, "Plasmid Vectors for High-Efficiency Expression Controlled by the P-Promoter OH Coliphage Lamda".
Klinkert et al. *Infect. Immun.* Aug. 1985 vol. 79(2) pp. 324–335, "Surface Proteins of *Mycoplasma hypopneumoniae* Identified from an *Eschenichoi coli* -Expression Plasmid Library".
Page 356 of *Molecular Biology of the Gene*, Third Edition, (J. D. Watson, pub'd by W. A. Benjamin, Inc., Menlo Park, Calif., (1976).
H. M. Geysen et al., *Proc. Natl. Acad. Sci. U.S.A.*, vol. 81, 3998–4002, (1984).
A. G. Alexander and G. E. Kenney, *Infect. Immun.*, 35, 937–942, (1982).
D. K. F. Chandler et al., *Infect. Immun.*, 35, 937–942, (1982).
J. Feldner et al., *Nature*, 298, 765–767, (1982).
S. J. Geary and E. M. Walczak, *Infect. Immun.*, 41, 132–136, (1983).
M. R. Hollingdale and R. M. Lemcke, *J. Hyg.*, 70, 85–98, (1971).
P. C. Hu et al., *Science*, 216, 313–315, (1982).
D. C. Krause et al., *Infect. Immun.*, 35, 809–817, (1982).
E. J. Nichols and G. E. Kenny, *Infect. Immun.*, 44, 355–363, (1984).
P. Whittlestone, *Adv. Vet. Sci. Comp. Med.*, 20, 277–307, (1976).
K. S. Wise and R. K. Watson, *Infect. Immun.*, 41, 1332–1339, (1983).
M. A. Taylor et al., *Proc. Natl. Acad. Sci. U.S.A.*, 80, 4154–4158, (1983).

*Primary Examiner*—Robin Teskin
*Attorney, Agent, or Firm*—James F. Haley, Jr.; Leon R. Yankwich

[57] ABSTRACT

Surface antigens of swine mycoplasma, such antigens prepared by recombinant DNA methods, a swine mycoplasma vaccine, based on such antigens, methods of treating swine to prevent enzootic pneumonia using that vaccine, and diagnostic tests based on these antigens or antibodies raised against them for detecting the presence of swine mycoplasma infections in swine herds, and DNA sequences that code for such antigens are disclosed.

11 Claims, 8 Drawing Sheets

FIG. 1

PME1921

```
        10          20          30          40          50          60
AAA TCC TTG TCA TGG GAT CCG GGG AAT TCG GGG AAC AAC AAT GAA AAA AAG AAA TAA
 K   S   L   S   W   D   P   G   N   S   G   N   N   N   E   K   K   K   -

70          80          90         100         110         120
TGC GTG ATT TTT TTG AAA GGG AAG AAA AGG CCT TTT TTT ATT ACC AGT TAT ATG GCC CTC

TTT TC ......
```

SINGLE LETTER AMINO ACID CODES

Phe: F   Leu: L   Ile: I   Met: M
Val: V   Ser: S   Pro: P   Thr: T
Ala: A   Tyr: Y   His: H   Gln: Q
Asn: N   Lys: K   Asp: D   Glu: E
Cys: C   Trp: W   Arg: R   Gly: G
       Termination: -  Unknown:

FIG.2

PME1922

```
              10            20            30            40            50            60
GGG AAT TCG GGA AAT AAT CCT GAA TCA AAA TCG CAA GAT AAT GCA AAT AAA GGA AAT TAT
 G   N   S   G   N   N   P   E   S   K   S   Q   D   N   A   N   K   G   N   Y
              70            80            90           100           110           120
CTT TCT TTA AAT ATT GGT TAT CGT AGT TTT GCT GAT AAA CCT GAC TTG CTG ATG GTT TTA
 L   S   L   N   I   G   Y   R   S   F   A   D   K   P   D   L   L   M   V   L
             130           140           150           160           170           180
TTA CAG TCC CAA AAG TTG GTA AAG AAC TTA GTA AAT CGA CAA TTA TGG CTG ATC CTG TCC
 L   Q   S   Q   K   L   V   K   N   L   V   N   R   Q   L   W   L   I   L   S
             190           200           210           220           230           240
CAT AAA AAA CAG GTA AAA AAA GAG GTC ATC GAA AAC GGG CAA AAA ATA GCA AAA GAC CTT
 H   K   Q   V   K   K   E   V   I   E   N   G   Q   K   I   A   K   D   L
             250           260           270
GGT GAA CCC GAA TTC TCA TGT TTG ACA GCT TAT CAT CG
 G   E   P   E   F   S   C   L   T   A   Y   H
```

FIG.3

PME1925

```
                     10              20              30              40              50              60
GGG AAT TCA AAG ATG AGT TTA AAA AAT ACT GAA CCT AAT TTT TTT GTC GGC ATC TAT GAA
 G   N   S   K   M   S   L   K   N   T   E   P   N   F   F   V   G   I   Y   E
                     70              80              90             100             110             120
AAG GCA ATT GAT AAA CGT TTT TCT TTG ATA GAT AAA ATT AAA ATC GCC CGA ATT CGG GCC
 K   A   I   D   K   R   F   S   L   I   D   K   I   K   I   A   R   I   R   A
                    130             140             150
CGA ATT CGG GCC CGA ATT CGG GAA TTC TCA TGT TTG AC
 R   I   R   A   R   I   R   E   F   S   C   L
```

FIG. 4

PME2413

```
       10              20              30              40              50              60
GGG AAT TCG ACC GTA AGT GAA ACA CGT GAT TTT ATT CAA AAA TTT GAC ATT TTC TAT CAG
 G   N   S   T   V   S   E   T   R   D   F   I   Q   K   F   D   I   F   Y   Q 70              80              90             100             110             120
GAA AAT GTG GGC AAA ATC AAA GAA GAT TTA GAT TTT GCA ATA GCT CCA AGT TTT ATA TCT
 E   N   V   G   K   I   K   E   D   L   D   F   A   I   A   P   S   F   I   S 130             140             150             160             170             180
TTA TCA CTA ATT TCT AAG TCC TTG ACT AAA AAA TTA AAA GAA ATT GCT GCT CAA AAT CTT AGT
 L   S   L   I   S   K   S   L   T   K   K   L   K   E   I   A   A   Q   N   L   S 190             200             210             220             230             240
CAG TTT GAT TCA GGA GCC TTT ACT GGG GAA ATC AGT GGC AAA ATG CTG CAG GAT TTA GGG
 Q   F   D   S   G   A   F   T   G   E   I   S   G   K   M   L   Q   D   L   G 250             260             270             280
ACA AAA TAT GTA ATT CCC GAA TTC TCA TGT TTG ACA GCT TAT CAT CGA
 T   K   Y   V   I   P   E   F   S   C   L   T   A   Y   H   R
```

FIG.5

PME442

```
       10          20          30          40          50          60
GGG AAT TCT GGA CCT GTA TAT GGG CCA TTT TTA CCG GGC GAA GAT AAG CGC GAA CTC AAC
 G   N   S   G   P   V   Y   G   P   F   L   P   G   E   D   K   R   E   L   N 70          80          90         100         110         120
CCA ATT GTG GCA AAA AGT GCT AAT TCA ATC ACA ATT GAT CTT AAT ATT TTA TCG ATA ATA
 P   I   V   A   K   S   A   N   S   I   T   I   D   L   N   I   L   S   I   I 130         140         150         160         170
ACC AAA ACA AAA TTA TCA GAG AGA GTT GCA GCC TTA AGC AGA GTT GAA TTC
 T   K   T   K   L   S   E   R   V   A   A   L   S   R   V   E   F
```

DNA SEQUENCES CODING FOR *MYCOPLASMA HYPOPNEUMONIAE* SURFACE ANTIGENS, METHODS OF USE TO MAKE THE CORRESPONDING PROTEINS

The present invention relates to surface antigens of swine mycoplasma, to such antigens prepared by recombinant DNA methods, to swine mycoplasma vaccine, based on such antigens, to methods of treating swine to prevent enzootic pneumonia using that vaccine, and to diagnostic tests based on these antigens or antibodies raised against them for detecting the presence of swine mycoplasma infections in swine herds.

*Mycoplasma hyopneumoniae*, the most important swine disease in the world, is the causative agent of enzootic pneumonia in pigs. It is a chronic, non-fatal disease affecting pigs of all ages. Infected pigs show only mild symptoms of coughs and fever. However, the economic impact of the infection is significant because of reduced feed efficiency and reduced weight gain, the consequence of which is the marketing of undersized pigs and substantial economic loss. Until now, efforts to control the disease by vaccination or by establishing pathogen-free herds have not been successful.

The physical association of mycoplasmas with the host cell surface is the basis for the development and persistence of enzootic pneumonia. By identifying and characterizing those surface protein constituents of *Mycoplasma hyopneumoniae* that mediate attachment to the host cell, and in particular, those that elicit neutralizing antibodies during the course of an infection, the basis for a vaccine against enzootic pneumonia and a diagnostic test for enzootic pneumonia has now been provided.

Identifying the DNA sequences that code for the aforementioned surface proteins, also makes it possible, using appropriate expression vehicles, to form recombinant DNA molecules and to transform appropriate hosts (e.g., prokaryotic or eukaryotic hosts) with those recombinant DNA molecules. Culturing of the transformed hosts then permits the hosts to express the DNA sequences and to produce the desired mycoplasma surface proteins.

Administering the produced and subsequently isolated surface proteins, active ingredients or combinations thereof to swine (e.g., by injection), in an amount sufficient to elicit the formation of antibodies, provides a means for immunizing swine against *Mycoplasma hyopneumoniae* infections. Effective carriers for such a vaccine and appropriate modes of administration are well known to those skilled in the veterinary arts.

The surface antigens of the present invention also form the basis for a diagnostic kit that is useful in testing swine herds for *Mycoplasma hyopneumoniae* infections. For example, using a diagnostic kit based on antibodies raised against one or more of the surface antigens of this invention, one of every ten or twenty swine in a herd could be tested routinely and frequently for the presence of mycoplasma infection. A positive test would then permit early vaccination of the entire herd with the antigens of this invention to prevent the spread of the mycloplasma.

The present invention also relates to polypeptides or peptides which are portions of a bacterial surface protein of *Mycoplasma hyopneumoniae* and which when administered to a swine elicit the formation of antibodies that bind to *Mycoplasma hyopneumoniae*.

Preferred polypeptides are selected from the group consisting of
NNNNEKKK;
NNPESKSQDNANKGNYLSLNIGYRS-
FADKPDLLMVLLQSQKLVKNLVNRQLW
LILSHKKQVKKEVIENGQKIAKDLGE;
NSKMSLKNTEPNFFVGIYEKAIDKRFSLID-
KIKI;
NSTVSETRDFIQKFDIFYQENVGKIKEDL-
DFAIAPSFISLSLISKSLTKKLE
NLSQFDSGAFTGEISGKMLQDLGTKYVI; and
RVEE.
NSGPVYGPFLPGEDKRELNPIVAKSAN-
SITIDLNILSIITKTKLSERVAALS The amino acids represented by the single letter amino acid codes used above are as follows:

| Phe: | F | Leu: | L | Ile: | I | Met: | M |
| Val: | V | Ser: | S | Pro: | P | Thr: | T |
| Ala: | A | Tyr: | Y | His: | H | Gln: | Q |
| Asn: | N | Lys: | K | Asp: | D | Glu: | E |
| Cys: | C | Trp: | W | Arg: | R | Gly: | G |

The present invention also relates to recombinant DNA molecules that are useful in preparing the aforementioned peptides. Preferred recombinant DNA molecules are characterized by a DNA sequence selected from the group consisting of
GAACAACAACCAAT-
GAAAAAAGAAATAATGCGT-
GATTTTTTTGAAAGGGAA
GAAAAGGCCTTTTTTTATTACCAGT-
TATATGGCCCTCTTTTC;
AAATAATCCTGAATCAAAATC-
GCAAGATAATGCAAATAAAGGAAAT-
TATCTT TTCTTTAAATATTGGTTATC-
GTAGTTTTGCTGATAAACCTGACTTGCT-
GATGG TTTTATTACAGTCCCAAAAGTTG-
GTAAAGAACTTAGTAAATCGACAATTATG
GCTGATCCTGTCCCATAAAAAAACAGG-
TAAAAAAGAGGTCATCGAAAACGGG
CAAAAAATAGCAAAAGACCTTGGTGAA;
GAATTCAAAGATGAGTTTAAAATATACT-
GAACCTAATTTTTTTGTCGGCATC TAT-
GAAAAGGCAATTGATAAACGTTTTTCTTT-
GATAGATAAAATTAAAATCG;
GATTCGACCGTAAGTGAAACACGTGATTT-
TATTCAAAAATTTGACATTTTC TATCAG-
GAAAATGTGGGCAAAATCAAAGAAGATT-
TAGATTTTGCAATAGCTC CAAGTTT-
TATATCTTTATCACTAATTTCTAAGTCCTT-
GACTAAAAAATTAGA AATTGCTGCT-
CAAAATCTTAGTCAGTTTGATTCAG-
GAGCCTTTACTGGGGAA ATCAGTG-
GCAAAATGCTGCAGGATTTAGG-
GACAAAATATGTAATT;
GAATTCTGGACCTGTATATGGGCCATTTT-
TACCGGGCGAAGATAAGCGCGAA
CTCAACCCAATTGTGGCAAAAAGTG-
CTAATTCAATCACAATTGATCTTAATA
TTTTATCGATAATAACCAAAAACAAAAT-
TATCAGAGAGAGTTGCAGCCTTAAG CA-
GAGTTGAATTC;

DNA sequences that hybridize to any of those DNA sequences and that code on expression for a surface antigen of *Mycoplasma hyopneumonia;* DNA sequences that code on expression for a surface antigen of *Myco-* plasma hyopneumonia coded on expression by any of the foregoing DNA sequences; and DNA sequences which are degenerate as a result of the genetic code to the aforementioned DNA sequences and which code for a surface antigen of Mycoplasma hyopneumonia.

BRIEF DESCRIPTION OF THE DRAWINGS

FIG. 1 depicts the relevant portions of the translated DNA sequence of recombinant DNA molecule PME 1921. The FIG. also depicts, using single letter amino acid codes, the relevant portions of the amino acid sequence of the fusion protein produced on expression of PME 1921. The underscored portions of both the DNA sequence and amino acid sequence represent the portions specifically derived from *Mycoplasma hyopneumoniae*. The remaining DNA and amino acid sequences displayed in FIG. 1 are derived from the expression vector and linkers used to clone the Mycoplasma sequences. FIG. 1 also depicts the single letter amino acid codes used herein.

FIG. 2 depicts the relevant portions of the translated DNA sequence of recombinant DNA molecule PME 1922. The Figure also depicts the amino acid sequence coded on expression by that relevant DNA sequence. Again, the underscoring is used to delineate the portions of the DNA and amino acid sequences derived from *Mycoplasma hyopneumonia*. The remaining sequences are derived from the expression vector and linkers.

FIG. 3 depicts the relevant portions of the translated DNA sequence of recombinant DNA molecule PME 1925. The Figure also depicts the amino acid sequence coded on expression by that relevant DNA sequence. Again, the underscoring is used to delineate the portions of the DNA and amino acid sequences derived from *Mycoplasma hyopneumoñiae*. The remaining sequences are derived from the expression vector and linkers.

FIG. 4 depicts the relevant portions of the translated DNA sequences of recombinant DNA molecule PME 2413. The Figure also depicts the amino acid sequence coded on expression by that relevant DNA sequence. Again, the underscoring is used to delineate the portions of the DNA and amino acid sequences derived from *Mycoplasma hyopneumonia*. The remaining sequences are derived from the expression vector and linkers.

FIG. 5 depicts the relevant portions of the translated DNA sequences of recombinant DNA molecule PME 442. The Figure also depicts the amino acid sequences coded on expression by that relevant DNA sequence. Again, the underscoring is used to delineate the portions of the DNA and amino acid sequences derived from *Mycoplasma hyopneumonia*. The remaining sequences are derived from the expression vector and linkers.

Figure 6:
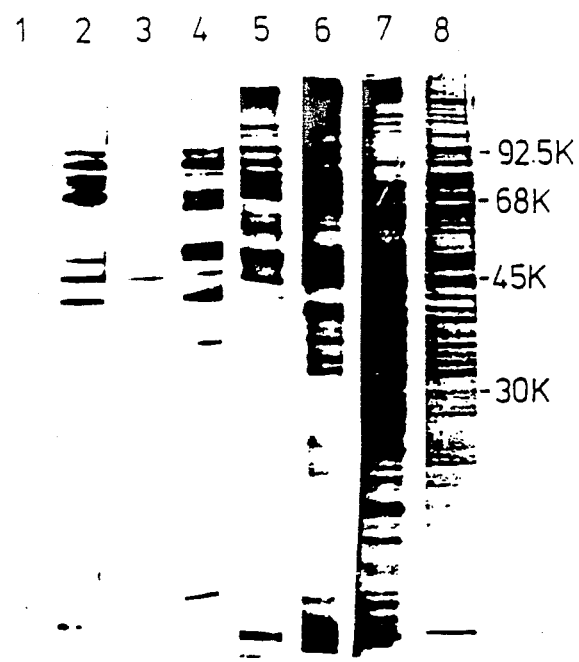
FIG. 6 illustrates the specificity of the pig antisera 19 and 20. Mycoplasma proteins were separated by PAGE, transferred to nitrocellulose paper and treated with the following sera: antiserum 19 (lane 2), antiserum 20 (lane 4), preimmune sera to antisera 19 and 20 respectively (lanes 1 and 3). These were compared to autoradiographs of protein gels where intact mycoplasmas were labeled with [$^{125}$I](lane 5), sonicated mycoplasma extract labeled in vigro with [$^{125}$I] (lane 6), and total mycoplasma proteins labeled in vivo with [$^{35}$S]-methionine (lane 7). Total mycoplasma proteins stained with Coomassie Blue are shown in lane 8. The molecular weights ($10^3$) are indicated on the right using molecular weight standards (Sigma).

As we have described above, this invention is characterized by surface antigens to *Mycoplasma hyopneumonia*. More particularly, it relates to surface antigens that confer immunity to that infection in treated swine, or are useful in the diagnosis of that infection.

The surface antitens of this invention comprise a genus of polypeptides and peptides that display the antigenicity of native *Mycoplasma hyopneumonia* surface antigens. Accordingly, among the surface antigens of this invention are recombinant polypeptides produced in hosts transformed by DNA sequences coding for those surface antigens. It should of course be understood that these polypeptides may include residues that are not related to *M. hyopneumonia*. For example, the recombinant polypeptides of this invention may be fusion proteins containing a protein portion derived from an expression vector or other source and a protein portion derived from *Mycoplasma hyopeneumonia*. These recombinant polypeptides and fusions of them may also include a starting methionine. All that is required is that the final polypeptides display the antigenicity of a native *mycoplasma hyopneumonia* surface antigen as defined above.

Also among the surface antigens of this invention are peptide fragments, synthetic or recombinant, of the above-described polypeptides. Such peptides are characterized by one or more of the surface antigenic sites that characterize these surface antigens. Those sites may be determined and the peptides containing them may be produced in a variety of ways. See, e.g., European Patent Application 83301589.4, Publication Number 0 090 581, published Oct. 5, 1983, and "Use Of Peptide Synthesis To Probe Viral Antigens For Epitomes To A Resolution of A Single Amino Acid" by H. M Geysen et al., Proc. Natl. Acad. Sci USA, Vol. 81 3998–4002 (1984), the disclosures of which are hereby incorporated herein by reference.

The surface antigens of this invention may also include mutants of the above described peptides or polypeptides. Such mutations, either at the DNA or amino acid level, may be useful in improving the yield of the antigens, their immunogenicity or antigenicity, or their compatibility with various purification schemes, adjuvants and modes of administration.

Finally, the surface antigens of this invention may be combinations of antigens or antigenic sites either on the same compound or in a mixture of compounds. These combinations may, of course, be derived from any of the above-described classes of surface antigens in accordance with this invention.

Referring now to FIGS. 1 to 5, we have depicted therein various surface antigens within the defined class of this invention. For example, each of those Figures displays a fusion protein comprising a portion derived from the expression vector and its linkers and a portion derived from *M. hyopneumonia.* Yet, each fusion product displays the required antigenicity of the surface antigen of this invention. It should also be understood that the *M. hyopneumonia* portions of those fusion products alone also display those antigenic characteristics and are also within the scope of this invention. Therefore, such polypeptides made by well known recombinant or synthetic techniques are also part of this invention. Similar peptides based on the antigenic sites carried by those polypeptides could also be prepared and employed without departing from the scope of this invention. Finally, the mycoplasma DNA sequences depicted in FIGS. 1 to 5 (the portions underscored) are useful in accordance with this invention as hybridization probes to select the DNA sequences coding for other surface antigens to *Mycoplasma hyopneumonia* and to select the complete, or at least more complete, DNA sequence coding for the antigens of which the depicted amino acid sequences are a part. These DNA sequences may then be used in substantially the same way as the DNA sequences of FIGS. 1 to 5 to prepare surface antigen of this invention. Thus each of the DNA sequences depicted in FIGS. 1 to 5, each of the underscored portions of those sequences and DNA sequences selected by them are within the scope of this invention.

In the cloning and expression of DNA sequences encoding the surface antigens of *Mycoplasma hyopneumonia* a wide variety of vectors are useful. These include, for example, vectors consisting of segments of chromosomal, non-chromosomal and synthetic DNA sequences, such as various known derivatives of SV40, known bacterial plasmids, e.g., plasmids from *E.coli* including col El, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and filamentous single stranded DNA phages, yeast plasmids such as the 2μ plasmid or derivatives thereof, and vectors derived from combinations of plasmids and phage DNAs, such as plasmids which have been modified to employ phage DNA or other expression control sequences.

Within each specific cloning or expression vehicle, various sites may be selected for insertion of the DNA sequences of this invention. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragment by alternative means.

For expression of the DNA sequences of this invention, these DNA sequences are operatively-linked to one or more expression control sequences in the expression vector. Such operative linking, which may be effected before or after the chosen DNA sequence is inserted into a cloning vehicle, enables the expression control sequences to control and promote the expression of the inserted DNA sequence.

Any of the wide variety of expression control sequences—sequences that control the expression of a DNA sequence when operatively linked to it—may be used in these vectors to express the DNA sequence of this invention. Such useful expression control sequences, include, for example, the early and late promoters of SV40, the lac system, the trp system, the TAC or TRC system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, and other sequences known to control the expression of genes of prokaryctic or eukaryotic cells or their viruses, and various combinations thereof. In mammalian cells, it is additionally possible to amplify the expression units by linking the gene to that coding for dehydrofolate reductase and applying a selection to host Chinese hamster ovary cells.

The vector or expression vehicle, and in particular the sites chosen therein for insertion of the selected DNA fragment and the expression control sequence employed in this invention are determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site for a particular phospholipase inhibitor protein sequence is determined by a balance of these factors, not all selections being equally effective for a given case.

In the preferred embodiments of this invention, we employ an expression control sequence derived from bacteriophage λ(P$_L$), the bacterial plasmid pEx29, a derivative of pBR322 and the Eco RI site to insert our DNA sequence into the plasmid for cloning and expression.

The recombinant DNA molecule containing the desired gene operatively linked to an expression control sequence may then be employed to transform a wide variety of appropriate hosts so as to permit such hosts (transformants) to express the gene, or fragment thereof, and to produce the polypeptide, or portion thereof, for which the hybrid DNA codes. The recombinant DNA molecule may also be employed to transform a host so as to permit that host on replication to produce additional recombinant DNA molecules as a source of *Mycloplasma hyopneumoniae* genes and fragments thereof.

A wide variety of hosts are also useful in producing the antigens and DNA sequences of this invention. These hosts include, for example, bacteria, such as *E.coli*, Bacillus and Streptomyces, fungi, such as yeasts, and animal, such as CHO cells, and plant cells in tissue culture.

The selection of an appropriate host for either of these uses is controlled by a number of factors recognized by the art. These include, for example, compatibility with the chosen vector, toxicity of the co-products, ease of recovery of the desired polypeptide, expression characteristics, biosafety and costs. No absolute choice of host may be made for a particular recombinant DNA molecule or polypeptide from any of these factors alone. Instead, a balance of these factors must be struck with the realization that not all hosts may be equally effective for expression of a particular recombinant DNA molecule. In the preferred embodiment of this invention, we employed *E.coli* GC1 which included the plasmid pcI857, a plasmid carrying the gene coding for resistance to kanamycin and also the temperature sensitive repressor for λ cI.

As we have previously demonstrated, it should be understood that the DNA sequences that are inserted at the selected site of a cloning or expression vehicle may include nucleotides which are not part of the actual gene coding for the desired polypeptide or may include only a fragment of the entire gene for that protein. It is only required that whatever DNA sequence is employed, the transformed host produces a polypeptide of the present invention. For example, the DNA sequences of this invention may be fused in the same reading frame in an expression vector of this invention to a portion of a DNA sequence coding for at least one eukaryotic or prokaryotic carrier protein or a DNA sequence coding for at least one eukaryotic or prokaryotic signal sequence, or combinations thereof. Such constructions may aid in expression of the desired DNA sequence, improve purification or permit secretion, and preferably maturation, of the desired polypeptide from the host cell. The DNA sequence may alternatively include an ATG start codon, alone or together with other codons, fused directly to the sequence encoding the first amino acid of a desired polypeptide. Such constructions enable the production of, for example, a methionyl or other peptidyl polypeptide, that is part of this invention. This N-terminal methionine or peptide may then be cleaved intra- or extra-cellularly by a variety of known processes or the polypeptide used together with the methionine or other fusion attached to it in the compositions and methods of this invention.

USE OF THE SURFACE ANTIGENS OF THE INVENTION IN DETECTING THE PRESENCE OF MYCOPLASMA HYOPNEUMONIAE INFECTION IN SWINE

The polypeptides and peptides displaying *Mycoplasma hyopneumoniae* antigenicity of this invention may be used in methods and kits designed to detect the presence of *Mycoplasma pneumoniae* infection in swine herds and therefore to recognize swine in a herd which have been infected by this virus, in order to permit early vaccination of the herd against the infection.

For example, the surface antigens produced by hosts transformed by recombinant DNA molecules of this invention, or antibodies raised against them, can be used in radio-immunoassay or ELISA (enzyme linked immunosorbent assay) for these purposes. In one type of radio-immunoassay, antibody against one or more of the surface antigens of this invention, raised in a laboratory animal (e.g., rabbits), is attached to a solid phase, for example, the inside of a test tube. Surface antigen is then added to the tube so as to bind with the antibody. A sample of swine serum, taken from 1 of each 10 to 20 swine per herd, together with a known amount of surface antigen antibody labelled with a radioactive isotope, such as radioactive iodine, is then added to the tube coated with the antigen-antibody complex. Any surface antigen (a marker for *M. hyopneumoniae* infection) antibody in the swine serum will compete with the labelled antibody for the free binding sites on antigen-antibody complex. Once the serum has been allowed to interact, the excess liquid is removed, the test tube washed, and the amount of radioactivity measured. A positive result, i.e., that the tested swine's serum contains *M. hyopneumonia* antibody, is indicated by a low radioactive count.

In one type of ELISA test, a microtitre plate is coated with one or more surface antigens of this invention and to this is added a sample of swine serum, again, from 1 in every 10 or 20 swine in a herd. After a period of incubation permitting interaction of any antibody present in the serum with the antigen, the plate is washed and a preparation of surface antigen antibodies, raised in a laboratory animal, and which are linked to an enzyme label is added, incubated to allow reaction to take place, and the plate is then rewashed. Thereafter, enzyme substrate is added to the microtitre plate and incubated for a period of time to allow the enzyme to work on the substrate, and the adsorbance of the final preparation is measured. A large change in adsorbance indicates a positive result, i.e., the tested swine serum had antibodies to *M. hyopneumonia* and was infected with that virus. USE OF THE SURF

USE OF THE SURFACE ANTIGENS OF THIS INVENTION IN VACCINES AGAINST *MYCOPLASMA HYOPNEUMONIAE* INFECTIONS

Standard methods known to those skilled in the art may be used in preparing the vaccine of the present invention for administration to swine. For example, the polypeptide of choice may be dissolved in sterile saline solution. For long term storage, the polypeptide may be lyophilized and then reconstituted with sterile saline solution shortly before administration. Prior to lyophilization, preservatives and other standard additives such as those to provide bulk, e.g., glycine or sodium chloride, may be added. A compatible adjuvant may also be administered with the vaccine.

A vaccine in accordance with this invention could also be prepared using antibodies raised against the polypeptides of this invention in laboratory animals, such as rabbits. This "passive" vaccine could then be administered to swine to protect them from *Mycoplasma hyopneumonia* infection.

The vaccine of the present invention is preferably dissolved in sterile saline solution and administered by injection at a dose of several mg of peptide per swine. The vaccine is preferably administered at 1 to 2 weeks of age and is preferably followed by a re-vaccination or booster at 4 to 6 weeks of age.

EXAMPLES
MATERIAL AND METHODS
GROWTH OF M. HYOPNEUMONIAE

We obtained *M. Hyopneumoniae* ATCC 27719 from the American Type Culture Collection. We grew the organisms in Friis medium (N. F. Friis, Nord. Vet. Med. 27, 337–339 (1975)) at 37° C. Culture stocks stored at −70° C. were used to inoculate the medium at a 1:10 dilution. We harvested the mycoplasmas at mid-log phase ($2-5\times10^7$ cells/ml), as evidenced by a slight orange-yellow colour shift of the medium. The culture was centrifuged at $12,500\times g$ for 15 min. at 4° C., washed twice in PBS (150 mM NaCl, 10 mM sodium phosphate buffer, pH 7.4), and suspended in PBS in 1/100th the original volume.

LABELING OF MYCOPLASMA PROTEINS

Lactoperoxidase-catalysed iodination of *M. hyopneumoniae* surface proteins were performed by the procedure of J. J. Marchalonis et al. (Biochem, J., 124, 921–927 (1971)). A 20 ml mid-log phase culture was washed twice in PBS, and suspended in 0.6 ml PBS. 0.3 ml of the suspension was pre-treated by sonication ($5\times15$ s) and served as a control. The labeling of whole cells and sonicated cells was carried out by the addition of the reagents (dissolved in PBS) in amounts and in sequence as follows: 5 µl KI ($5\times10^{-5}$ M, Merck), 10 µl lactoperoxidase (0.2 mg/ml, Sigma), 50 µCi carrier-free [$^{125}$I](New England Nuclear Corp.) and 3 µl $H_2O_2$ ($9\times10^{-4}$ M). After 5 min, another 3 µl of added and the reaction continued for 5 more min. Sample buffer was then added to the radioiodinated samples before gel electrophoresis.

Labeling of total mycoplasma proteins with [$^{32}$S]-methionine was performed with 20 ml cultures grown in Friis medium in the presence of 250 µCi [$^{32}$S]-methionine (Amersham). Cells were harvested at mid-log phase and protein extracts prepared as before.

DNA ISOLATION

Genomic DNA was isolated from our culture of *M. Hyopneumoniae* substantially as described by Blin and Stafford (Nucleic Acids Res., 3, 2303–2308 (1976)) for the isolation of DNA from eukaryotic cells.

SDS-POLYACRYLAMIDE GEL ELECTROPHORESIS (PAGE) AND WESTERN BLOTTING

*E.coli* extracts or mycoplasms lysates were subjected to PAGE by the method of Laemmli (*Nature*, 227, 680–685 (1970)). The Western blot procedure was carried out according to Towbin et al. (Proc. Nat. Acad. Sci. USA, 76, 4350–4354 (1979)). Proteins separated on the gels were transferred electrophoretically to nitrocellulose paper (overnight at 4° C., at 60V/0.3A in 192 mM glycine, 25 mM Tris-HCl (pH 8.3) and 20% methanol), using a Transblot apparatus (Biorad) and identified with antiserum and radioiodinated protein A.

PREPARATION OF ANTISERA

A 10-week old pig, free from mycoplasma infection was intranasally inoculated with freshly grown *M. Hyopneumoniae* culture ($2\times10^7$ cells for each immunization) at intervals of 2 to 4 weeks for a period of 3 months. Sera were collected a week prior to each inoculation; antiserum taken after the sixth inoculation (antiserum 19) was used for the subsequently described immunological screening. A second pig, also 10 weeks of age, was injected once intramuscularly with $2\times10^7$ organisms emulsified in Freund's complete adjuvant. Antiserum taken 3 weeks thereafter (antiserum 20) was also used for immunological screening.

To analyze the specificity of these antisera for mycoplasma surface antigens we used a Western blot. We first separated total Mycoplasma proteins by PAGE, as described above, transferred to nitrocellulose paper and treated with antisera 19 and 20, as well as preimmune antisera to both. The results are displayed in FIG. 6 (Lane 1—preimmune serum to antiserum 19; Lane 2—antiserum 19; lane 3—preimmune serum to antiserum 20; lane 4—antiserum 20; lane 8—total Mycoplasma protein stained with Coomassie Blue). As shown in FIG. 6, our antisera recognized only a defined group of about 11 proteins from the total mycoplasma proteins.

In order to demonstrate that the mycoplasma proteins specifically recognized by these antisera were located on the cell surface, our Western blot of total mycoplasma proteins was compared to autoradiographs of [$^{125}$I]-labeled proteins of intact mycoplasmas iodinated by the lactoperoxidase method because such iodination is confined to cell surface proteins (FIG. 6, lane 5). As shown in FIG. 6, lane 5, many of the proteins that reacted with both antisera in our Western blot also comigrated with those that were iodinated in the intact bacteria. This demonstrates that our antisera are specific to cell surface proteins.

We also compared the iodination of intact mycoplasmas with iodination of a sonicated cell extract (FIG. 6, lane 6) or total mycoplasma proteins labelled in vivo with [$^{35}$S-methionine] (FIG. 6, lane 7). In Contrast to the labeling of intact cells, where only a discrete number of proteins was labeled (approximately 10), iodination of the cell extract and labelling of total cell proteins resulted in the labeling of many more proteins, whose profile is similar to total mycoplasma proteins stained with Coomassie Blue (FIG. 6, lane 8). Thus it was concluded that our antisera were mainly directed against cell surface components and bind predominantly to the outside of the mycopasma membrane.

CLONING OF MYCOPLASMA DNA FRAGMENTS

We decided to clone our Mycopasma DNA directly into an expression vector and then to screen the resulting library for expression of mycoplasma surface antigen using the antibodies prepared above.

20µg of mycoplasma genomic DNA (prepared as above) were digested with 2 ng of DNAseI (Boehringer, Mannheim) in 200µl buffer containing 33 mM Tris-HCl (pH 7.6), 10 mM MnCl$_2$, 1 mM β-mercaptoethanol for 5 min at room temperature, giving fragments approximately 100–1000 bp long (average about 300 bp). After filling in the ends of the fragments with *E.coli* polymerase I, [$^{32}$P]-labeled EcoRI linkers were added. The mycoplasma DNA was then cleaved with EcoRI and ligated into the EcoRI siteoof expression vector pEx29.

Figure 7:
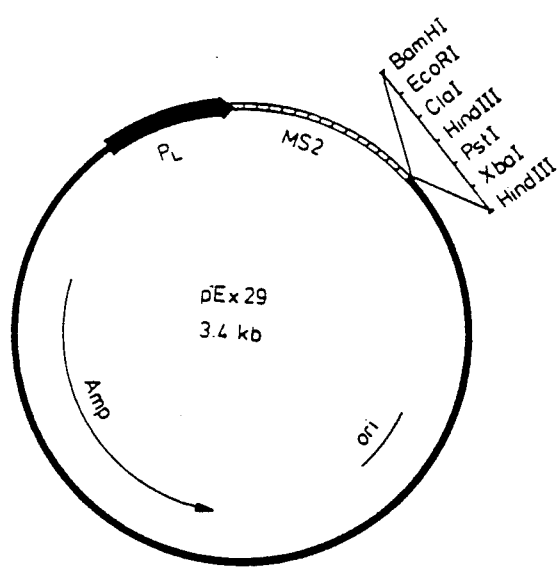
FIG. 7 depicts expression vector pEx29 used for constructing the preferred genomic library this invention. It is a derivative of the expression vector pPlc24. The original EcoR1 site between the PL promoter and the MS2 region (encoding 100 N-terminus amino acids) was deleted and a polylinker was introduced into the BamHI and HindIII sites, as indicated. The origin of replication (ori) and the region coding for β-lactamase (Amp) are indicated.

Expression vector pEx29 (E. Beck, unpublished results) is a derivative of pPLc24 [E. Remaut et al., *Gene*, 15, pp. 81–93 (1981): E. Remaut et al., *Gene*, 22, pp. 103–113 (1983)]. As depicted in FIG. 7, pEx29, as compared to pPLc24, has the original EcoRl site between PL and the MS2 region (encoding 100 N-terminal amino acids) deleted and a polylinker introduced into the Bam HI and Hind III sites. The expression vector, like pPLc24, carries the gene coding for β-lactamase (ampicillin resistance).

1 pMol DNA (calculated from the radioactivity of added linkers) ligated to 1 pMol vector resulted in approximately $5 \times 10^4$ transformants; approximately 75% of the cones carried inserts.

*E.coli* strain GCl (T. F. Meyer, Cell, 30, 45–52 (1982)) (a gift of T. F. Meyer), was grown to a density of $4–7 \times 10^7$ cells/ml at 28° C. and prepared for transformation according to the procedure of D. Hanahan (*J.Mol. Biol.*, 166, 557–580, 1983). The strain, transformed with plasmid pcI857, a plasmid carrying a kanamycin resistante marker and a temperature-sensitive λ cI repressor gene (E. Remaut et al., *Gene*, 22, 103–113 (1983)), which regulates expression from the PL promoter, was then used as a cloning and expression host for pEx29 carrying our mycoplasma DNA inserts. Expression of our mycoplasma DNA in this expression vector is represented in the presence of pcI857 at 28° C. while induction is achieved by incubating the culture at 42° C. Translation initiation in pEx29 is provided by a ribosome binding site from MS2 polymerase (see FIG. 6). Expression of DNA inserted at the EcoRI site of pEx29 produces a Iusion protein consisting of 100 N-terminal amino acids from MS2, any amino acids coded for by the linker, and the amino acids coded for by the DNA that occurs before any in phase stop codon and if there is no stop codon in the inserted DNA, any additional amino acids coded for by the following linker and vector sequences that precede the first in-phase stop codon.

IMMUNOSCREENING OF THE GENOMIC LIBRARY

Approximately $3 \times 10^5$ transformants grown at 28° C. on twenty 25 cm×25 cm agar plates to colonies 1 mm in diameter, were transferred to nitrocelulose filters. Immediately after transfer, the filters were placed onto prewarmed agar plates and incubated at 42° C. for 2 h. The colonies were lysed by a 15 min exposure to chloroform vapour. The filters were then air-dried for 30 min, soaked for 2 h in PBS, containing 2% BSA (bovine serum albumin), and incubated overnight with antiserum 19 (diluted 1:500 in PBS, 1% BSA, 0.01% NP40). Before incubation, we had absorbed the antiserum with an *E.coli* extract to reduce any background staining of our colonies. The filters were washed in PBS containing 0.05% NP40, incubated for 4 h with [$^{125}$I]-labeled protein A and rinsed extensivey with PBS, 0.05% NP40. Clones showing positive signals on autoradiograms were picked in duplicate and re-screened by the same procedure.

Approximately 40 clones gave positive signals of different intensifies. Ten of these clones were finally selected for further analysis on the basis that they expressed proteins, in quantities up to 10% to 20% of the total proteins synthesized. The rest of the clones provided either fusions that were synthesized only in small amounts (<10%) or were unstable. Thus, these clones were not further characterized. Of course, it should be understood that the other selected classes contain DNA sequences that code for Mycoplasma cell surface antigen. Accordingly, they, and others selected by the process of this invention, are part of this invention. For subsequent analysis, these classes may be treated similarly to the ten selected. They may also be sequenced for comparison with the selected classes and used in a variety of expression vectors to produce the antigens coded for by them.

EXPRESSION OF FUSION PROTEINS IN *E.COLI*

The ten selected clones were grown at 28° C. in LB medium, containing 50 μg ampicillin/ml and 25 μg kanamycin/ml, to a density of $2 \times 10^9$ cells/ml. Expression was then induced by incubating the culture (diluted 1:5 in prewarmed medium) at 42° C. for 2 h under vigorous aeration (H. Küpper, (Proc. of the Fourth Int. Symp. On Genetics of Industrial Microorganisms, 222–226 (1982)). 0.5 ml bacteria samples (corresponding to $2 \times 10^8$ cells) were pelleted, suspended in an equal volume of sample buffer (4% SDS (sodium dodecyl sulfate), 125mM Tris-HCl (pH 6.8), 10% β-mercaptoethanol, 10% glycerol and 0.02% bromphenol blue), boiled for 5 min and analysed on 12.5% SDS-polyacrylamide gels (U.K. Laemmli, *Nature*, 227, 680–685 (1970)).

Figure 8:
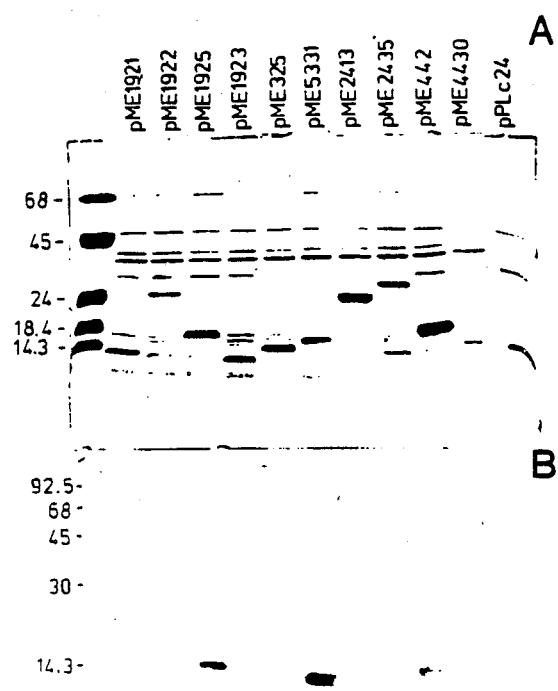
FIG. 8 illustrates the specificity of the fusion proteins expressed in *E.coli*. (A) Total cell extracts of the ten clones selected from the immunoscreening of the library were analysed by PAGE and stained with Coomassie Blue. pPlc24itself expresses an 11K protein corresponding to the N-terminus of the MS2 polymerase (outmost right). (B) After fractionating total cell extracts by PAGE as above, the fractionated proteins were transferred to nitrocellulose filters and incubated with antiserum 19. Bound antibody was detected with [$^{125}$I]Protein A and autoradiographed. Fusion proteins were seen to react with the antiserum in varying intensities, apparently independent of the quaniities of fusion proteins synthesized. The [$^{14}$C]-labeled molecular weight standards (NEN Corp.) are shown on the left.

FIG. 8(A) shows a Coomassie Blue stained gel of total cell extracts of these ten chosen *E.coli* clones. The Figure also shows a Coomassie Blue stained extract from purified plasmid pPlc24, itself, which expresses an 11 K protein corresponding to the N-terminus of MS2 polymrase. FIG. 8(B) shows a Western blot of the chosen cell extracts using antiserum 19 and [$^{125}$I]-labelled protein A, as described above. As shown in FIG. 8(B), the fusion proteins reacted with the antiserum with varying intensities. In order to prepare arger amounts of these proteins, 20 ml overnight cultures grown at 28° C. were diluted in 180 ml medium and incubated a 42° C. for 2 h shaking vigorously. The cells were pelleted and washed in 30 ml 50mM Tris-HCl(pH 8), 100mM NaCl and resuspended in 1.6 ml 10% sucrose, 50mM Tris-HCl (pH 8). After addition of 0.4 ml lysozyme (5 mg/ml) and 0.4 ml 0.5M EDTA, the Cells were incubated at 37° C. for 30 min. Thereafter, 4 ml Triton lytic mix (0.1% Triton X-100, 50mM Tris-HCl (pH 8), 72.5mM EDTA) were added, the mixture kept for 15 min on ice and further incubated for 30 min at 37° C. The cells were then sonicated (4×15 s) and centrifuged for 30 min at 20,000xg. The pellet was suspended first in 5 ml 1M urea and extracted for 30 min at 37° C., then centrifuged and further extracted with 5 ml 7M urea (30 min, 37° C.). The fusion protein solubilized in the 7M urea supernatant was then further purified on a 12.5% preparative SDS-polyarylamide gel.

The fusion protein band was visualised by staining for 10 min with Coomassie Blue (0.06% Coomassie Brilliant Blue, 50% methanol and 10% acetic acid) and excised. The gel was crushed and the protein eluted overnight at 42° C. with PBS containing 0.1% SDS. Polyacrylamide was separated from the original protein by centrifugation and the supernatant containing the fusion protein was concentrated to 1 mg/ml. The average yield from a 20 ml overnight culture was between 0.2-1 mg of protein.

IDENTIFICATION OF SPECIFIC MYCOPLASMA PROTEINS USING ANTI-FUSION PROTEIN ANTISERA RAISED IN RABBITS

Antisera against our above-described MS2-mycoplasma fusion proteins were produced in rabbits. A total of 200-500 μg of gel purified protein was used for each animal spread over 3 subcutaneous injections in 2-3 weekly intervals. The first injection was in Freund's complete adjuvant. The subsequent injections employed Freund's incomplete adjuvant. After 3 months, antiserum was collected and used for Western blot anayses. The titers of the various antisera obtained were between $1:10^3$ to $1:10^4$ in an ELISA test.

Figure 9:
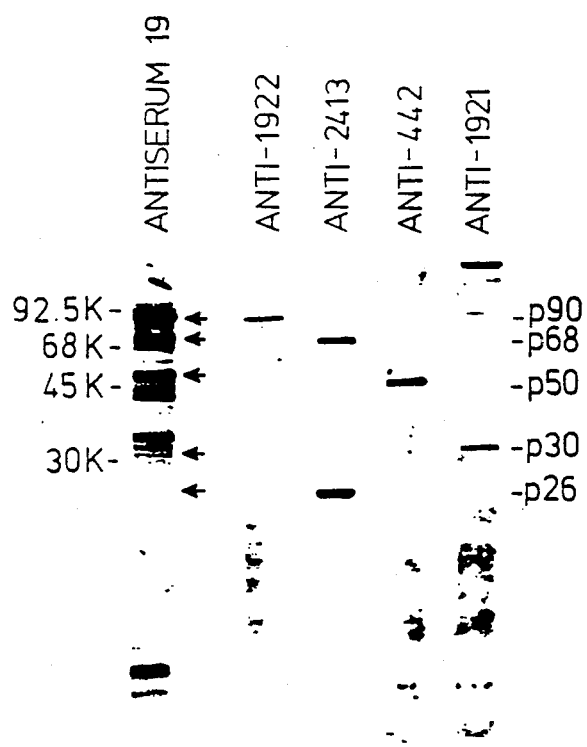
FIG. 9 depicts Western blots of *M. hyopneumoniae* proteins using specific antisera. Nitrocellulose strips prepared as described in FIG. 1 were treated with various antisera. The mycoplasma profile stained by antiserum 19 was used as a reference. Mycoplasma proteins recognized by antisera raised against various of the surface antigens of this invention are indicated by the arrows; their approximate molecular weights being shown on the right based on comparison with molecular weight standards (left).

The antisera were tested by Western blot analyses of M. hyopneumonia total cell proteins for the presence of antibodies against specific mycoplasma proteins. FIG. 9 shows the results for four of the prepared antisera: Anti-1922 reacted primarily with a protein designated p90 according to its molecular weight of 90,000; anti-2413 reacted essentially with two proteins, p68 and p26 (molecular weights 68,000 and 26,000, respectively), while anti-442 recognized p50 (molecular weight 50,000). Anti-1921 recognized a protein with a molecular weight of 30,000, termed p30. Anti-1925 also reacted with a protein of the same molecular weight (not shown in FIG. 9). All these proteins comigrated with the mycoplasma bands stained strongly by antiserum 19, indicated by the arrows in the figure, except for p26, which correlated only to a minor band. Pre-immune sera from rabbits immunized with the various fusion proteins did not stain any mycoplasma proteins (not shown in FIG. 9). These results demonstrate that our mycoplasma antigens have induced specific antibodies capable of reacting with discrete M. hyopneumoniae cell surface antigens.

We also correlated the mycoplasma surface proteins recognized by the antisera prepared against our surface antigens with those that were sensitive to a trypsin digestion and, therefore, presumably on the mycoplasma cell surface.

As a control, we first prepared 20 ml of a fresh mycoplasma culture. We then centrifuged the culture, washed it once with PBS and suspended it in 2 ml PBS. 1 ml of this suspension was incubated with 50 μg trypsin. To the remaining 1 ml, which acted as control, no trypsin was added. After a 10 min incubation at room temperature, the cells in both tubes were centrifuged, washed once with PBS, the pellets suspended in sample buffer and loaded onto polyacrylamide gels. The separated proteins were stained with Coomassie Blue or transferred to nitrocelulose paper for Western blotting. The results are displayed in FIG. 10.

Figure 10:
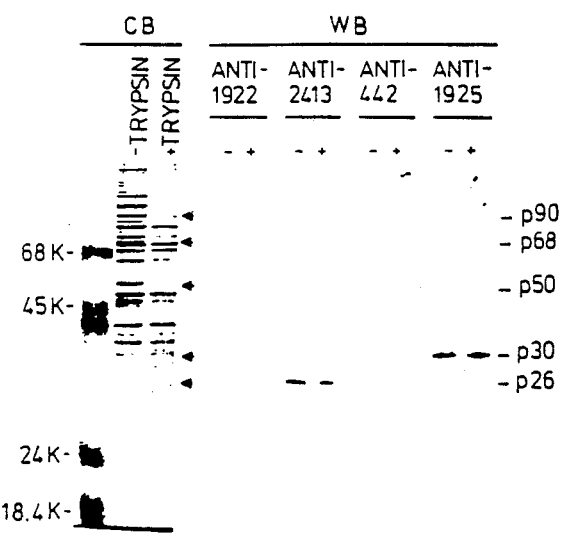
FIG. 10 depicts trypsin sensitivity of the cloned surface antigens of this invention. Intact mycoplasma cells (corresponding to 1 ml culture) were incubated in the absence or presence of trypsin (50μg/ml) and the proteins thereafter separated by PAGE and either stained with Coomassie Blue (CB) or transferred to nitrocellulose fiters for Western blot analyses (WB). The blots were incubated with antisera raised against various of our cloned antitens, as indicated; the arrows show the positions of the proteins that were recognized by the antisera.

As shown in FIG. 10 (CB), several high molecular weight proteins were selectively degraded by trypsin digestion to lower molecular weight ones. As also shown in FIG. 10 trypsin digestion eliminated the antigens associated with surface proteins p90, p68 and p50 that are specifically recognized by antisera to our surface antigens. Accordingly, these proteins recognized by our antisera are localized on the cell surface, with the more trypsin sensitive sites exposed to the outside. Two other proteins, p30 recognized by anti-1925 (FIG. 10) and anti-1921 (not shown), and p26 recognized by anti-2413 were not sensitive to trypsin digestion. This insensitivity of the p30 and p26 proteins to trypsin does not require that they be non-surface proteins because some surface proteins may be incorporated into the cell membrane such that they have no sites available for trypsin digestion. p30 also does not comigrate with an iodinated surface protein. Again, that is not clear proof that p30 is not a surface protein because p30 may represent a minor surface component or one too poor in tyrosine residues to be labeled well.

Both anti-1921 and anti-1925 recognize p30. Southern blotting has demonstrated that the DNA inserts of pME 1921 and 1925 belong to different restriction fragments. Because the DNA sequences of the two clones share no sequence homology, the two clones may correspond either to different regions of the same gene or to two different genes coding for proteins of the same molecular weight.

p26 on the other hand, coelectrophoreses with an iodinated protein and is weakly recognized by antiserum 19. Therefore, it is likely to be on the cell surface. p26 is also one of the two proteins, the other being p68, recognized by the anti-2413. These proteins could either be two unrelated proteins sharing a common antigenic determinant or p68 could be a precursor of p26. The second alternative is supported by Southern blot analysis which demonstrated that only one genomic fragment hybridizes to the pME2413 mycoplasm insert.

More direct evidence for the surface location of our cloned antigens was provided by in situ labeling of mycoplasmas with specific antibodies.

Frozen thin-sectioning and antibody labeling were carried out according to G. Griffiths et al. (Methods in Enzymol., 96, 466-485 (1983)). A mycoplasma cell pellet from a 10 ml culture was fixed in 4% formaldehyde, infused with 2.3M sucrose and frozen in liquid nitrogen. Sectioning was carried out with glass knives. Thin sections were thawed, transferred to Formvar/carbon-coated, 100 mesh copper grids and floated on 10 lμ IgG fractions (diluted 1:10 in 1% fetal calf serum in PBS), and incubated at room temperature for 30 min. The grids were rinsed 5 times with PBS for a total of 30 min, then transferred to a 5 μl drop of gold-protein A solution (1 mg/ml), diluted 1:30 in PBS, 10% fetal calf serum. The reaction was allowed to take place for 20 min at room temperature. The grids were further rinsed 5 times for 30 min in PBS, and finally 4 times for 5 min with distilled water. The grids were then stained with 2% uranyl acetate and embedded in a 1.5% methyl cellulose solution. Sections were then visualized in the electron microscope. The electron micrographs demonstrated the binding of antiserum 19, and to a lesser extent the binding of anti-1922 to the membrane of the mycoplasmas.

CHARACTERIZATION OF MYCOPLASMA CELL SURFACE ANTIGENS

To characterize our cell surface antigens further, we sequenced 5 of our clones (pME 1921, 1922, 1925, 2413 and 442) using conventional DNA sequencing methodology. The DNA sequences obtained, and the amino acid sequences derived from them, are displayed in FIGS. 1 to 5, respectively. Each of these FIGS. displays a portion of the expressed DNA sequence derived from the expression vector and linkers (and the amino acid sequence coded for by it) and the DNA sequence derived from M. hyopneumoniae (underscored) and its expression product. For example, in FIG. 1, nucleotides 1–32 (pME1921) are derived from the vector and linker and nucleotides 33–125 are derived from mycoplasma. However, only 8 mycoplasma amino acids are expressed because there is a stop codon in phase (nucleotides 57–60, FIG. 1). On the other hand, in pME1922, the entire mycoplasma insert is expressed because the first in phase stop codon occurs in the vector sequence at the carboxy terminal end of the mycoplasma insert of that clone.

The DNA and amino acid sequences of our 5 clones can be used in a variety of ways to prepare other surface antigens in accordance with this invention. For example, the specific mycoplasma coding sequences, or fragments of them, can be isolated from each of the clones and those sequences used in other expression vectors to produce the antigens coded for by them either as fusion proteins or as mycoplasma derived proteins only. These coding sequences or fragments can also be employed to prepare DNA probes (synthetic or from the clones themselves) and the probes used to screen other DNA libraries (cDNA or genomic) to select by hybridization substantially homologous DNA sequences that code for more complete versions of the antigens already coded for by our clones or DNA sequences that code for other related mycoplasma surface antigens. For example, a genomic library of longer DNA inserts prepared in a vector like λ gt10 or λ gt11 may be screened to select full length genes coding for those surface antigens. These genes may then be used as described above to express the antigens coded for by them in a wide variety of hosts and expression vectors.

Finally, the amino acid sequences derived from the DNA sequences of this invention may be used to prepare synthetic peptides containing the antigenic site or sites of our cell surface antigens. See, e.g., European Patent Application 83301589.4, Publication Number 0 090 581, pubished October 5, 1983; and H. M. Geysen et al., Proc. Natl. Acad. Sci. U.S.A., Vol. 81, 3998–4002 (1984). These synthetic peptides may then be used in vaccines and diagnostic tests substantially as described above.

DNA sequences, recombinant DNA molecules and transformed hosts according to this invention are exemplified by various micoorganism deposits made in the culture collection of the Deutsche Sammlung von Mikroorganism, Gottingen, West Germany, on March 19, 1985 as follows:

(1) E.coli GCl (pcI857) (pME1921) deposited as DSM 3271.

(2) E.coli GCl (pcI857) (pME1922) deposited as DSM 3272.

(3) E.coli GCl (pcI857) (pME1925) deposited as (4) E.coli GCl (pcI857) (pME2413) deposited as DSM 3274.

(5) E.coli GCl (pcI857) (pME442) deposited as DSM 3275.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A DNA sequence selected from the group consisting of
GAACAACAACAAT-GAAAAAAAGAAATAATGCGT-GATTTTTTTGAAAKGGGAAG AAAAGGCCTTTTTTTATTACCAGT-TATATGGCCCTCTTTTC;
AAATAATCCTGAATCAAAATC-GCAAGATAATGCAAATAAAGGAAAT-TATCTT TCTTTAAATATTGGTTATC-GTAGTTTTGCTGATAAACCTGACTTGCT-GATGG TTTTATTACAGTCCCAAAAGTTG-GTAAAGAACTTAGTAAATCGACAATTATG GCTGATCCTGTCCCATAAAAAACAGG-TAAAAAAGTCATCGAAAACGGG CAAAAAATAGCAAAGACCTTGGTGAA;
GAATTCAAAGATGAGTTTAAAAAATACT-GAACCTAATTTTTTTGTCGGCATC TAT-GAAAAGGCAATTGATAAACGTTTTTCTTT-GATAGATAAAATTAAAATCG;
GAATTCGACCGTAAGTGAAACACGTGATTT-TATTCAAAAATTTGACATTTTC TATCAG-GAAAATGTGGGCAAAATCAAAGAAGATT-TAGATTTTGCAATAGCTC CAAGTTT-TATATCTTTATCACTAATTCTAAGTCCTT-GACTAAAAAATTAGA AATTGCTGCT-CAAAATCTTAGTCAGTTTGATTCAG-GAGCCTTTACTGGGGAA ATCAGTG-GCAAAATGCTGCAGGATTTAGG-GACAAAATATGTAATT; and
GAATTCTGGACCTGTATATGGGCCATTTT-TACCGGGCGAAGATAAGCGCGAA CTCAACCCAATTGTGGCAAAAGTG-CTAATTCAATCACAATTGATCTTAATA TTTTATCGATAATAACCAAAACAAAAT-TATCAGAGAGAGTTGCAGCCTTAAG CA-GAGTTGAATTC.

2. A recombinant DNA molecule comprising a DNA sequence selected from the group consisting of
(a) the DNA sequences
GAACAACAATGAAAAAAAGAATAATGCGT-GATTTTTTTGAAAGGGAAGAAAAGGCCTT TTTTATTACCAGTTATATGGCCCTCTTTTC;
AAATAATCCTGAATCAAAATC-GCAAGATAATGCAAATAAAGGAAAT-TATCTT TCTTTAAATATTGGTTATC-GTAGTTTTGCT TTTTATTACAGTC-CCAAAAGTTGGTAAAGAACTTAG-TAAATCGACAATTATG TTGCTGATCCTGTCCCATAAAAAACAGG-TAAAAAACAGTAAA. AAAAGAGCTCATC-GAAAACGGGCAAAAAATAG-CAAAAGACCTTGTGAA;
GAATTCAAAGATGAGTTTAAAAAATACT-GAACCTAATTTTTTTGTCGGCATCTAT-GAAAAGG CAATT-GATAAACGTTTTTCTTTGATAGATAAAAT-TAAAATCG;
GAATTCGACCGTAAGTGAAAAIAGGT-GATTTTATTCAAAAATTTGACATTTT-CTATCAGGAAA ATGTGGGCAAAAAT-CAAAGAAAAATTTAGATTTT-GCATAGCTCCAAGTTTTATATCTT-TATCA CTAATTTCTAAGTCCTTGAC-TAAAAAATTAGAAATTGCTGCT-CAAAATCTTAGTCAGTTTGA TTCAG-GAGCCTTTACTGGGGAAATCAGTG- GCAAAATGCTGCAGGATTTAGG-
GACAAAATATG TAATT; and
GAATTCTGGACCTGTATATGGGCCATTTT-
TACCGGGCGAAGATAAGCGCGAACT-
CAACCCAA TTGTGGCAAAAAGTG-
CTAATTCAATCACAATTGATCT-
TAATATTTTATCGATAATAACCAAA
ACAAAATTATCAGAGAGATTGCAGCCT-
TAAGCAG.AGTTGAATTC; and (b) DNA sequences that code on expression for a surface antigen of *Mycoplasma hyopneumonia* coded for on expression by any of the foregoing DNA sequences.

3. A recombinant DNA molecule according to claim 2, wherein said DNA sequence is operatively linked to an expression control sequence in the recombinant DNA molecule.

4. A recombinant DNA molecule according to claim 3, wherein said expression control sequence is selected from the group consisting of the early and late promoters SV40[1 , the lac system, the TAC system, the TRC system, the trp system, major operator and promotor regions of phage λ the control regions of fd coat protein, the promoter for 3-phosphoglycerate kinase or other glycolytic enzymes, the promoters of acid phosphatase, the promoters of yeast α-mating factors, and other sequences which control the expression of genes of prokaryotic or eukaryotic cells or their viruses.

5. A recombinant DNA molecule according to claim 3 selected from the group consisting of pME1921, pME1922, pME1925, pME2413 and pME442.

6. A host transformed with the recombinant DNA molecule of any one of claims 2 to 5.

7. The transformed host according to claim 6, selected from the group consisting of strains of *E.coli*, Pseudomonas, Bacillus, yeasts, or other fungi, mouse, swine or other animal or plant hosts and human tissue cells.

8. The transformed host according to claim 7 wherein the *E.coli* is *E.coli* GC1.

9. The transformed host according to claim 8, wherein said host is selected from the group consisting of *E.coli* GC1 (pcI857) (pME1921), *E.coli* GC1 (pcI857) (pME1922), *E.coli* GC1 (pcI857) (pME1925), *E.coli* GC1 (pcI857) (pME2413), and *E.coli* GC1 (pcI857) (pME442).

10. A method of producing a polypeptide which when administered to a swine elicits the formation of antibodies that bind to *Mycoplasma hyopneunoniae*, said method comprising the step of culturing a host transformed with a recombinant DNA molecule according to any one of claims 3 to 5.

11. The method according to claim 10, wherein the host comprises strains of *E.coli*, Pseudomonas, Bacillus, yeast or other fungi, mouse, swine, or other animal or plant hosts and human tissue cells.

* * * * *